United States Patent [19]
Hamid et al.

[11] Patent Number: 5,963,317
[45] Date of Patent: Oct. 5, 1999

[54] APPARATUS FOR INSPECTING WELL SCREENS AND ASSOCIATED METHODS

[75] Inventors: Syed Hamid, Dallas; Darrell W. Adkins, Farmers Branch, both of Tex.

[73] Assignee: Halliburton Energy Services, Inc., Dallas, Tex.

[21] Appl. No.: 08/911,653

[22] Filed: Aug. 15, 1997

[51] Int. Cl.[6] .................................................... G01N 21/00
[52] U.S. Cl. ..................................... 356/239.1; 356/241.1
[58] Field of Search .................. 356/239.1, 241.1–241.6, 356/432

[56] References Cited

U.S. PATENT DOCUMENTS 5,777,730  7/1998  Dunlap ................................. 356/241.1

*Primary Examiner*—Robert H. Kim
*Assistant Examiner*—Amanda Merlino
*Attorney, Agent, or Firm*—William M. Imwalle; Marlin R. Smith

[57] ABSTRACT

Apparatus for inspecting well screens and associated methods of inspecting well screens provides accurate and convenient inspection of well screens. The methods and apparatus may also produce data useful in designing well completions. In a described embodiment, a method of inspecting a filtering portion of a well screen includes utilizing a light sensor to measure the intensity of light transmitted through the filtering portion. An array of fiber optic lines is arrayed about the filtering portion and interconnected to the sensor. A light source within the filtering portion and the array of fiber optic lines are displaced simultaneously along the filtering portion. The sensor is connected to an instrument, which indicates whether the measured light intensity is within an acceptable range. Furthermore, the measured light intensity may be related to a hydraulic resistance of the filtering portion.

43 Claims, 3 Drawing Sheets

APPARATUS FOR INSPECTING WELL SCREENS AND ASSOCIATED METHODS

BACKGROUND OF THE INVENTION

The present invention relates generally to screens utilized in subterranean wells and, in an embodiment described herein, more particularly provides apparatus for inspecting well screens and associated methods of inspecting well screens.

A typical well screen is generally tubular in shape and may be on the order of twenty or thirty feet in length. Very basically, the typical well screen includes a generally tubular filtering portion attached in an overlying relationship to a perforated tubular base pipe. The filtering portion operates to exclude sand and other particulate matter from entering a string of production tubing extending to the earth's surface. The base pipe facilitates interconnection of the well screen to the tubing string.

A variety of representative configurations of well screens may be found in a publication entitled HALLIBURTON SCREENS, published by Halliburton Energy Services of Duncan, Okla. The disclosure of this publication is incorporated herein by this reference. Therein it may be seen that well screen configurations include filtering portions which have a single wire wrapped jacket, multiple concentric wire wrapped jackets with gravel or graded sand between the jackets and a sintered metal sleeve. Wire wrapped jackets generally include a series of circumferentially spaced apart and longitudinally extending ribs, with a triangular or keystone-shaped wire helically wrapped about the ribs.

In use, it is important that the filtering portion of a well screen exclude sand or other particles from fluid flowing through the filtering portion. The filtering portion is manufactured to exclude a certain specified minimum size of particle, with the specified size varying depending upon the application. If particles larger than the specified size are not excluded by the filtering portion, they will enter the production tubing and may cause significant damage and economic loss during operation of the well. However, if the filtering portion is made to exclude too small a size particle, fluid flow therethrough will also be impeded and the filtering portion may easily become clogged with fine particles, reducing the rate of production from the well.

To prevent such damage and other economic loss, well screen manufacturers inspect their well screen filtering portions. Usually, this inspection is performed before the filtering portion is attached to the base pipe. Unfortunately, prior to the present invention, these inspections have been somewhat unreliable.

In one method of inspecting a wire wrapped jacket, a thickness gauge is inserted between adjacent wraps of wire to determine whether the wire wraps are properly spaced apart. If the wraps are spaced too far apart, large particles will be permitted to flow between the wraps. If the wraps are spaced too close together, a large resistance to fluid flow therethrough will result. It is, however, impractical to insert a thickness gauge between all wraps of a long well screen. Therefore, these insertions are typically done only at several selected places, leaving a significant part of the filtering portion essentially not inspected.

Another inspection technique, which is particularly useful with a filtering portion having multiple wire wrapped jackets and gravel therebetween (hereinafter referred to as a "prepacked" jacket), is to insert a light bulb within the filtering portion and look for excessive light passed through the prepacked jacket. Such excessive light may indicate that the inner and outer wire wrapped jackets are not concentric (thereby producing a thin layer of gravel therebetween on one side), the gravel is not tightly packed therebetween, the wire wraps on one or both of the wire wrapped jackets are too far apart, etc. Unfortunately, this method relies on the subjective determination of the person viewing the light and provides no quantitative basis on which to establish criteria for accepting or rejecting a particular filtering portion.

Additionally, neither of the above methods produces data which may be utilized to indicate a resistance to flow of fluid through the filtering portion. An indication of hydraulic resistance of the filtering portion would be useful in enabling a well operator to choose a well screen suited for desired particular flow characteristics of a well. Thus, the well operator would be given more control over the production and/or long term performance of the well.

From the foregoing, it can be seen that it would be quite desirable to provide a method of inspecting well screens which does not rely on spot checks of the filtering portion, and which does not rely on subjective determinations, but which permits filtering portions to be accurately and conveniently inspected. In addition, it would be desirable to produce an indication of the hydraulic resistance of a filtering portion as a result of the inspection. It is accordingly an object of the present invention to provide such a method and associated inspection apparatus.

SUMMARY OF THE INVENTION

In carrying out the principles of the present invention, in accordance with an embodiment thereof, apparatus is provided which permits a well screen to be inspected quantitatively. This reduces the chances for error in the inspection and allows data regarding characteristics of the well screen to be recorded and analyzed. Methods of inspecting well screens are also provided.

In broad terms, a method of inspecting well screens is provided which includes the steps of positioning a light source on one side of a filtering portion of a well screen and detecting the intensity of light transmitted through the filtering portion. Anomalies in the detected light intensity point to corresponding defects in the filtering portion. Additionally, the hydraulic resistance of the filtering portion may be determined from the detected light intensity.

In another aspect of the present invention, the intensity of the light transmitted through the filtering portion is detected by a light sensor. The light sensor may be positioned closely adjacent the filtering portion to directly detect the light intensity at a particular point on the filtering portion, or, for example, the sensor may be remotely located and interconnected via an array of fiber optic lines to a circumferentially and axially extending area of the filtering portion.

In yet another aspect of the present invention, the light source and light sensor or fiber optic array are attached to a displacement device. The displacement device displaces both the light source and the sensor or array across the filtering portion simultaneously. In this manner, the light source is maintained in a position opposite the light sensor or array.

In still another aspect of the present invention, the light sensor is interconnected to an instrument. The instrument is capable of receiving an output of the light sensor and indicating when the detected light intensity falls outside of an acceptable range. For example, the instrument may produce an audible or visual signal when the light intensity is unacceptable. The instrument may also record the light intensity and produce a written record of the inspection.

Furthermore, the instrument may be interconnected to the displacement device, so that the detected light intensity may be correlated to a position or specific surface area on the filtering portion.

Where a fiber optic array or other light conducting device is utilized, the individual fiber optic lines or other members may be arranged to enhance detection of the light transmitted through the filtering portion. For example, the fiber optic lines or other members may be helically arranged about the filtering portion to correspond with the pitch of the wire wraps. Additionally, a light intensifying device, such as a convex lens, may be positioned to focus the transmitted light on the light conducting device and thereby increase the intensity of light received by the light conducting device.

These and other features, advantages, benefits and objects of the present invention will become apparent to one of ordinary skill in the art upon careful consideration of the detailed description of representative embodiments of the invention hereinbelow and the accompanying drawings.

DETAILED DESCRIPTION

Figure 1:
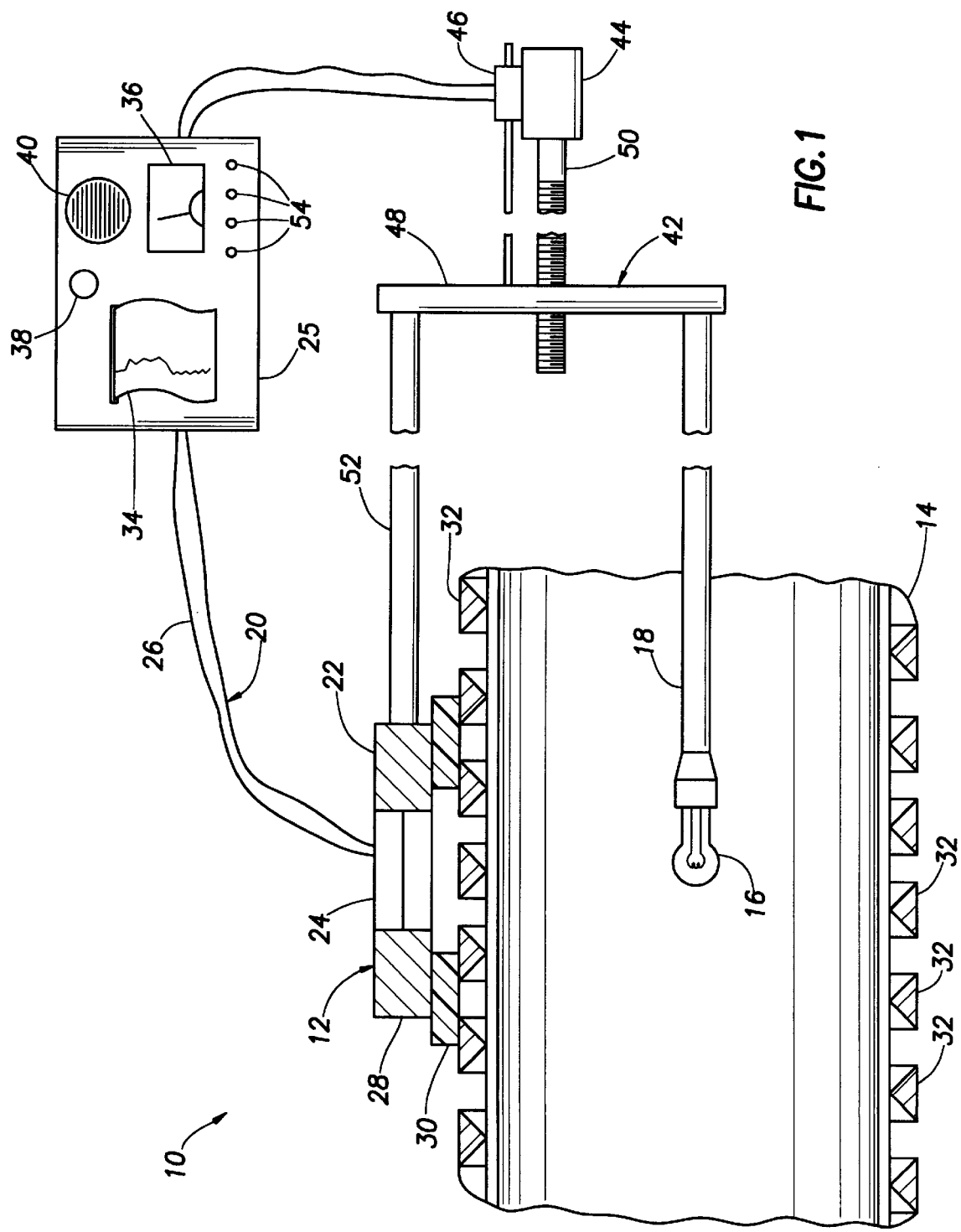
FIG. 1 is a schematic view of a first apparatus and method embodying principles of the present invention.

Representatively and schematically illustrated in FIG. 1 is a method 10 and apparatus 12 which embody principles of the present invention. In the following description of the method 10, apparatus 12, and other apparatus and methods described herein, directional terms, such as "above", "below", "upper", "lower", etc., are used for convenience in referring to the accompanying drawings. Additionally, it is to be understood that the various embodiments of the present invention described herein may be utilized in various orientations, such as inclined, inverted, horizontal, vertical, etc., without departing from the principles of the present invention.

The method 10 and apparatus 12 are representatively illustrated and described herein as utilized in an inspection of a single wire wrapped jacket or filtering portion 14 of a well screen. It is to be clearly understood, however, that the method 10 and apparatus 12 may be utilized in inspections of other types of filtering portions and well screens. For example, the method 10 and apparatus 12 may be utilized to inspect a prepacked jacket or sintered metal sleeve of a well screen.

The apparatus 12 includes a light source 16. The light source 16 is representatively illustrated as an incandescent light bulb, but it may alternatively be a halogen lamp, a fluorescent bulb, a light emitting diode, a laser, or any other source of light. The applicants have successfully utilized a 300 watt incandescent bulb for this purpose.

The light source 16 is installed in a fixture 18 which extends axially within the filtering portion 14, only a longitudinal portion of which is depicted in FIG. 1. The fixture 18 may include devices (not shown) for centralizing the light source within the filtering portion 14. The fixture 18 may also serve as a conduit for power lines used to supply power to the light source 16, or to store batteries for powering the light source, etc.

The apparatus 12 also includes a light intensity measuring device 20. The device 20 includes a light receiving device 22 interconnected to an instrument 25. The light receiving device 22 includes a light receiving member or light sensor 24. The light sensor 24 may be any of a variety of sensors which are capable of sensing the intensity of light received therein and producing an output related to that intensity. For example, the light sensor 24 may be a photoelectric cell as representatively illustrated in FIG. 1, with its output available on lines 26 interconnected thereto.

The light receiving device 22 also includes a housing 28 in which the sensor 24 is mounted. The housing 28 is complementarily shaped relative to the outer side surface of the filtering portion 14. A flexible gasket or other shield 30 is attached to the housing 28 to restrict the entrance of ambient light into the housing 28.

Preferably, the housing 28 spaces the sensor 24 away from the filtering portion 14 in a position that maximizes its reception of light passed through the filtering portion 14. In this regard, note that the sensor 24 should not be positioned too close to the wire wraps 32, or the wire wraps will cast shadows on the sensor. The sensor 24 should be spaced sufficiently far from the wire wraps 32 so that the light passed between the wire wraps 32 overlaps outside of the wire wraps before it is received by the sensor. This spacing is dependent upon the geometry of the filtering portion 14, but may be easily determined with minimal experimentation. Of course, if the apparatus 12 is used to inspect a sintered metal sleeve, these considerations still apply, except that no wire wraps are present.

It will now be readily appreciated by a person with ordinary skill in the art that the apparatus 12 permits light to be directed through a sidewall of the filtering portion 14 and the intensity of the light to be sensed after it has passed through the sidewall. It will also be readily appreciated that the intensity of the sensed light will vary depending on characteristics of the filtering portion 14. For example, if wraps of wire 32 on the filtering portion 14 are spaced closer together, the sensed light intensity will decrease because less light will be permitted to pass between the wire wraps, and if the wraps of wire are spaced farther apart, the sensed light intensity will increase.

Thus, the filtering portion 14 may be inspected by comparing the light intensity sensed by the sensor 24 with a desired light intensity or range of light intensity. This desired light intensity or range of light intensity may be easily determined by using the apparatus 12 with a filtering portion 14 having the desired wire wrap spacing, or with filtering portions having a desired range of wire wrap spacings. For example, if a well screen manufacturer determines that a particular well screen should have a wire wrap spacing range of 0.010–0.012 in., filtering portions 14 may be prepared, one of which has a 0.010 in. wire wrap spacing and another of which has a 0.012 in. spacing. The apparatus 12 may then be installed on each of the filtering portions 14 and the sensed light intensities recorded. Thereafter, the manufacturer will be able to conveniently inspect filtering portions by comparing their sensed light intensities using the apparatus 12 with the recorded acceptable range of light intensities. Alternatively, an acceptable maximum or minimum light intensity may be recorded and the sensed light intensity compared to the maximum or minimum value.

For indicating and recording the sensed light intensities, the representatively illustrated instrument 25 includes a chart recorder 34, a meter 36, a light 38 and a speaker 40. It is to be clearly understood that it is not necessary for the instrument 25 to include all or any one of these indicating and recording means. For example, the instrument 25 may have nothing more than a digital readout (not shown), or another combination of indicating and/or recording means.

The light 38 and/or speaker 40 are useful in indicating whether a sensed light intensity is within an acceptable range, or is greater than a maximum or less than a minimum acceptable light intensity. For example, if the filtering portion 14 is being inspected to determine whether its wire wraps 32 are spaced too far apart, the instrument 25 may be configured so that the light 38 lights and/or the speaker 40 sounds when the sensed light intensity exceeds a maximum acceptable light intensity corresponding to the maximum acceptable spacing of the wire wraps.

The meter 36 and/or chart recorder 34 are useful in indicating the sensed light intensity. The sensed light intensity may be viewed directly on the meter 36 and/or derived from the written record provided by the chart recorder 34. The chart recorder 34 also permits the sensed light intensity to be displayed as a function of another variable, such as time or distance. Of course, other displaying means, such as a monitor, may be utilized without departing from the principles of the present invention.

It will be readily appreciated that the light receiving device 22 and light source 16 may be repositioned relative to the filtering portion 14 to thereby perform an inspection on another part of the filtering portion sidewall. Preferably, the light source 16 and light receiving device 22 are repositioned opposite each other relative to the filtering portion 14, so that there is no change in their relative spacings, orientation, etc. that would influence the sensed light intensity. Additionally, the light source 16 and light receiving device 22 may be displaced synchronously or simultaneously, so that an area of the filtering portion 14 may be conveniently and expeditiously inspected. For these purposes, the apparatus 12 includes a displacement device 42.

The representatively illustrated displacement device 42 includes a motor 44, a displacement sensor 46, a yoke 48, a threaded rod 50 threadedly received in the yoke and an elongated member 52 interconnecting the light receiving device 22 and the yoke 48. The fixture 18 is attached to the yoke 48. Thus, displacement of the yoke 48 will cause simultaneous displacement of both the light source 16 and the light receiving device 22.

When the motor 44 is operated, the threaded rod 50 rotates and causes displacement of the yoke 48. Therefore, the distance the light source 16 and light receiving device 22 displace relative to the filtering portion 14 is directly related to the speed of the motor 44 and the amount of time the motor is operated. This distance may be measured by the displacement sensor 46, which may be any of a variety of commercially available sensors, such as a linear variable displacement transducer, a motor rotation counter, etc.

The motor 44 and sensor 46 are interconnected to the instrument 25 in the representatively illustrated apparatus 12. The instrument 25 includes switches, knobs, slides, etc. 54 for supplying power to the light source 16, supplying power to the motor 44, adjusting gain for outputs of the sensors 24, 46, etc. Thus, the instrument may be configured and programmed to automatically perform an inspection of the filtering portion 14 by turning on the light source 16 and motor 44, thereby displacing the light source and light receiving device 22 relative to the filtering portion, and indicating the light intensity sensed by the sensor 24.

Additionally, the chart recorder 34 may produce a plot of sensed light intensity as a function of distance along the filtering portion 14, using the outputs of the sensors 24, 46.

Of course, it is not necessary for the instrument 25 to include any or all of these controls 54 or to be so configured and programmed, and the instrument may include other controls and be otherwise configured and programmed without departing from the principles of the present invention. It will be readily appreciated that the instrument 25 may easily be configured and programmed as described herein by a technician using commercially available components and without undue experimentation.

Although the apparatus 12 is representatively illustrated in FIG. 1 as including various elements which enhance its efficiency, accuracy and convenience of use, it will be readily appreciated that an inspection of the filtering portion 14 may be accomplished according to the principles of the present invention without the need of some of these elements. For example, the light source 16 and light receiving device 22 may be displaced synchronously relative to the filtering portion 14 by simply tying each end of a rope to one of them and pulling the rope. Thus, it is not necessary for the apparatus 12 to include any or all of the illustrated elements thereof, and the apparatus may include other elements not shown or described herein.

Figure 2:
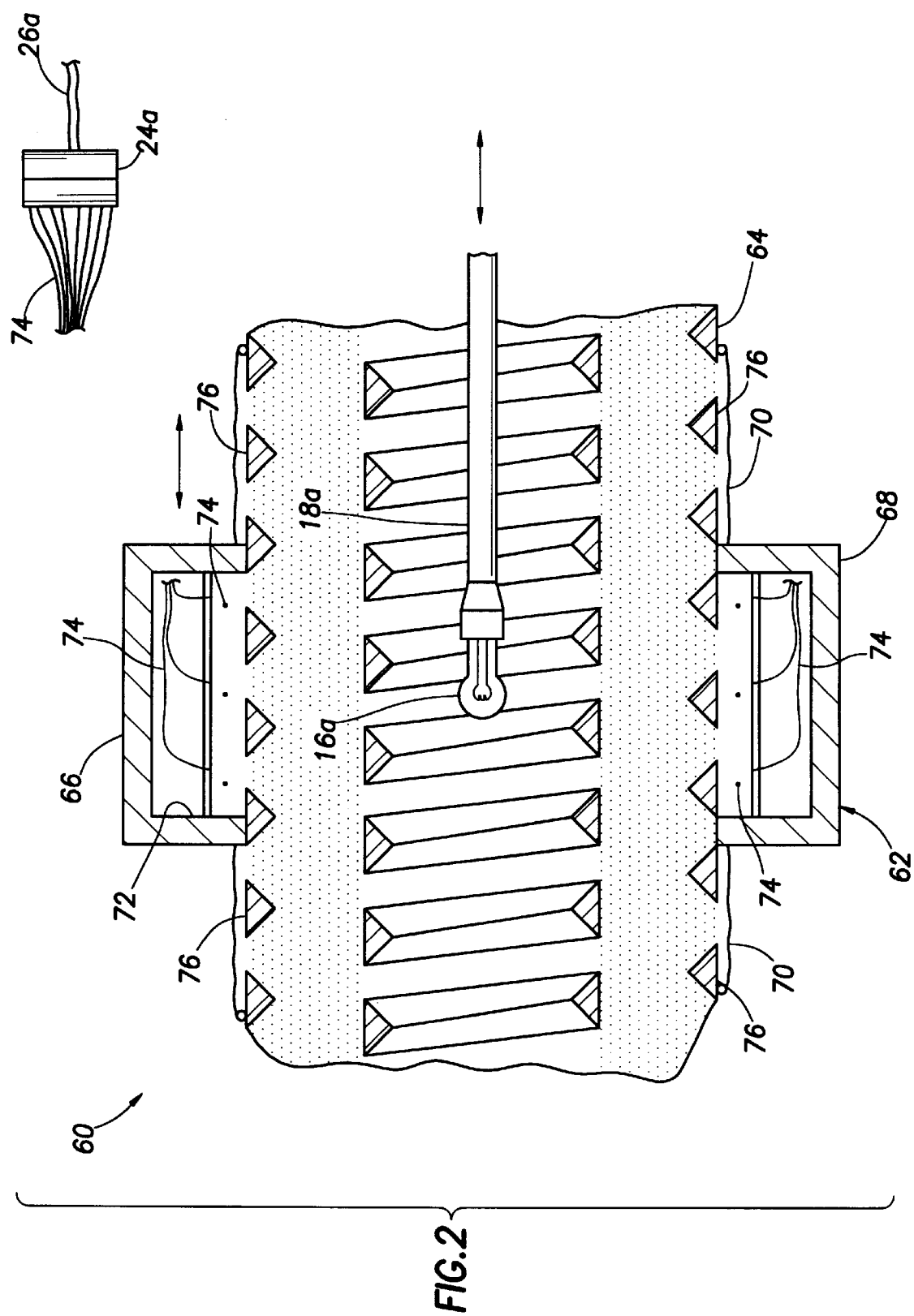
FIG. 2 is a schematic view of a second apparatus and method embodying principles of the present invention.

Referring additionally now to FIG. 2, another method 60 and apparatus 62 embodying principles of the present invention are schematically and representatively illustrated. Elements of the apparatus 62 which are similar to those previously described are indicated in FIG. 2 using the same reference numbers, with an added suffix "a". In FIG. 2, the method 60 and apparatus 62 are shown as used in an inspection of a prepacked well screen filtering portion 64. However, it is to be clearly understood that the method 60 and apparatus 64 may be utilized in inspections of other types of well screens and filtering portions, such as sintered metal sleeves and single wire wrapped jackets, without departing from the principles of the present invention.

The depicted apparatus 62 differs from the previously described apparatus 12 in part in that a light receiving device 66 of the apparatus 62 does not include the light sensor 24a mounted to a housing 68 thereof. Instead, the light sensor 24a is remotely located relative to the housing 68. Another significant difference is that the housing 68 circumferentially surrounds the filtering portion 64, so that the light receiving device 66 is capable of receiving light directed through a circumferentially extending area of the filtering portion at one time.

The housing 68 is complementarily shaped relative to the outer side surface of the filtering portion 64. Axially and circumferentially extending cloth shrouds 70 are attached to the housing 68 at either axial end of the housing to restrict entrance of ambient light into the housing. Thus, the housing 68 is generally annular-shaped and has an interior annular cavity 72 formed therein which is open to the filtering portion 64.

Mounted within the cavity 72 is an axially and circumferentially extending array of light conducting members or fiber optic lines 74. The fiber optic lines 74 serve as individual light receiving members for receiving the light transmitted through the filtering portion 64. The fiber optic lines 74 conduct the light to the light sensor 24a, which is connected to an instrument, such as the previously described instrument 25. Of course, although the sensor 24a is depicted as being located remote from the housing 68, it may also be mounted within the cavity 72, or otherwise located, without departing from the principles of the present invention. Additionally, the fiber optic lines 74 may be divided into portions, and each portion connected to a separate sensor, or multiple sensors without fiber optic lines connected thereto may be positioned circumferentially about the filtering portion 64, without departing from the principles of the present invention.

The fiber optic lines 74 in the representatively illustrated apparatus 62 are helically positioned about the filtering portion 64 to correspond with a pitch of wire wraps 76 of the filtering portion. This array of the fiber optic lines 74 may be otherwise configured without departing from the principles of the present invention.

The light receiving device 66 and light source 16a are attached to a displacement device, such as the previously described displacement device 42. It will be readily appreciated that, by displacing the light source 16a and light receiving device 66 axially relative to the filtering portion 64, the entire filtering portion may be conveniently and efficiently inspected. Note that the method 60 permits several characteristics of the filtering portion 64 to be simultaneously inspected. For example, if the gaps between wire wraps 76 of either of the inner or outer jackets of the filtering portion 64 are not within an acceptable range, the light intensity sensed by the sensor 24a will also not be within an acceptable range. Similarly, if the thickness of the gravel between the inner and outer jackets is not within an acceptable range (such as, if the jackets are not concentric), or the gravel is not packed sufficiently or includes voids, the sensed light intensity will also not be within an acceptable range.

Figure 3:
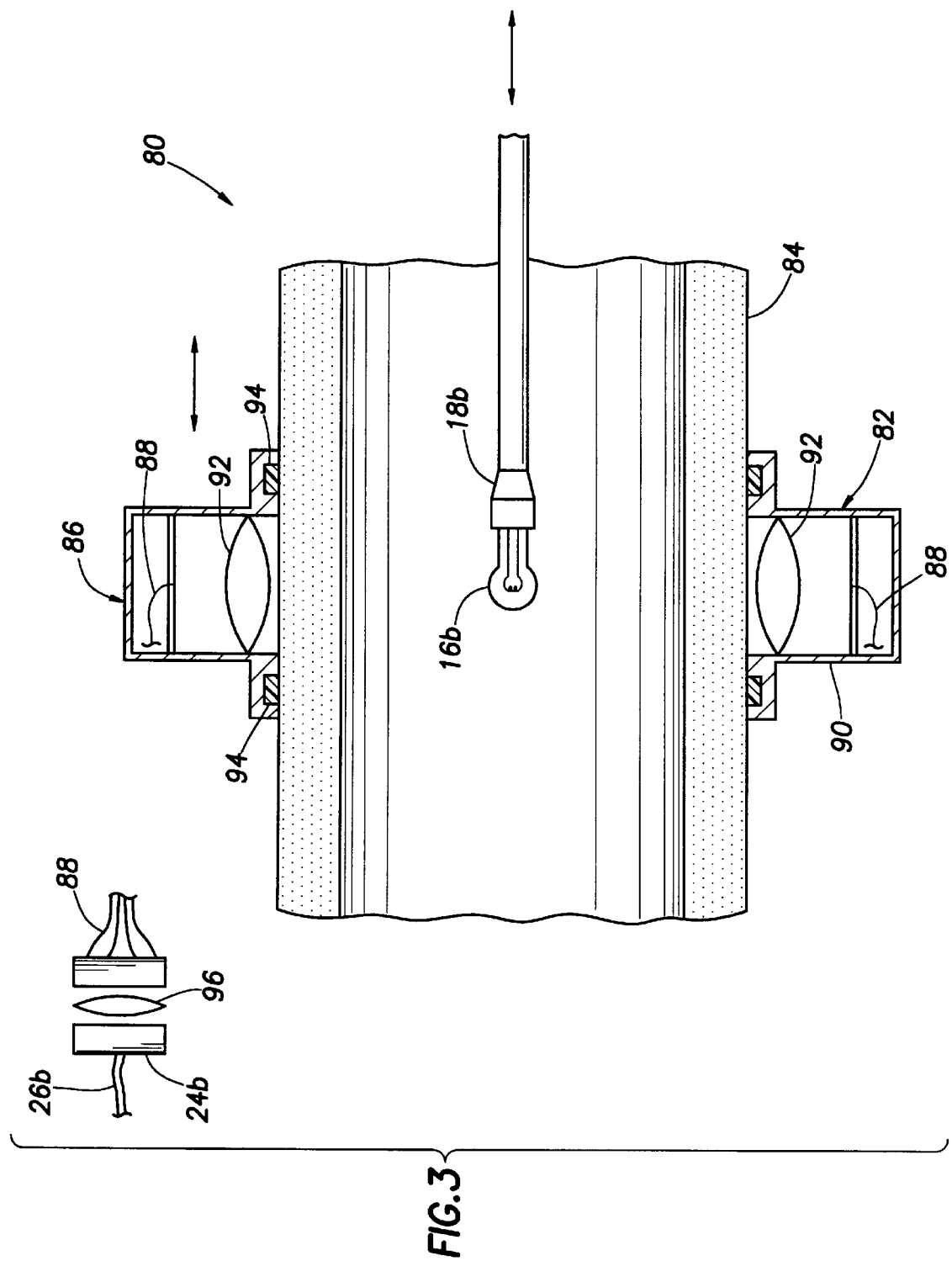
FIG. 3 is a schematic view of a third apparatus and method embodying principles of the present invention.

Referring additionally now to FIG. 3, still another method 80 and apparatus 82 for inspecting well screens embodying principles of the present invention are representatively and schematically illustrated. Elements of the apparatus 82 which are similar to those previously described are indicated in FIG. 3 using the same reference numbers, with an added suffix "b". In FIG. 3, the method 80 and apparatus 82 are shown as used in an inspection of a sintered metal sleeve filtering portion 84. However, it is to be clearly understood that the method 80 and apparatus 84 may be utilized in inspections of other types of well screens and filtering portions, such as prepacked jackets, wire mesh jackets, and single wire wrapped jackets, without departing from the principles of the present invention.

The apparatus 82 differs from those previously described in part in that a light receiving device 86 thereof includes a relatively small array of light conducting members or fiber optic lines 88 mounted within its housing 90. Resilient circumferential gaskets 94 restrict ambient light from entering the housing 90. Light transmitted from the light source 16b through a sidewall portion of the filtering portion 84 is focused on each of the fiber optic lines 88 by a light intensifying member 92.

The light intensifying members 92 are representatively illustrated as convex lenses, but it is to be understood that one or more other types of light intensifying members may be utilized in the apparatus 82 without departing from the principles of the present invention. Thus, the light receiving device 86 includes a circumferentially spaced apart series of the lenses 92, which focus the transmitted light on a corresponding series of circumferentially spaced apart fiber optic lines 88. This reduces the number of fiber optic lines 88 needed to adequately conduct the transmitted light to the light sensor 24b.

In place of, or in addition to, the lenses 92, the apparatus 82 may include a light intensifying member or lens 96 interposed between the fiber optic lines 88 and the light sensor 24b. The lens 96 focuses the light conducted by the fiber optic lines 88 on the sensor 24b to ensure that sufficient light is sensed by the sensor 24b.

The light receiving device 86 and the light source 16b are displaced relative to the filtering portion 84 as previously described for the apparatus 12, 62 in the corresponding methods 10, 60. In this way, the entire filtering portion 84 is conveniently and efficiently inspected by comparing the sensed light intensity with an acceptable range of light intensities or with a minimum or maximum acceptable light intensity. For the sintered metal filtering portion 84, a relatively high sensed light intensity may indicate a lack of concentricity, a thin area, excessively large pores, etc. Note that these characteristics are simultaneously evaluated by the apparatus 82 and method 80.

Light intensities sensed by any of the methods 10, 60, 80 described herein may be easily correlated to a hydraulic resistance of the particular filtering portion being inspected. In this manner, a hydraulic resistance for each filtering portion inspected may be recorded to aid in selecting a desired well screen for installation in a particular well. The influence of manufacturing techniques on the hydraulic resistances of well screens may be easily evaluated. Well operators may specify well screens by their hydraulic resistance, which directly relates to rate of production from a well, rather than by particular well screen configuration, and manufacturers of well screens may certify that their well screens meet these specifications. These and other benefits of measuring the hydraulic resistance of a well screen during its inspection will be readily appreciated by a person of ordinary skill in the art.

To correlate hydraulic resistance to a sensed light intensity, the filtering portion of a particular well screen configuration may be inspected to determine its sensed light intensity. The hydraulic resistance of the well screen may then be measured in test conditions simulating known well conditions, such as by flowing fluid at a known differential pressure and flow rate through the well screen. These correlations may be made for different well screen configurations, sizes, etc.

Of course, modifications, additions, deletions, substitutions, and other changes may be easily made to the above described methods 10, 60, 80 and apparatus 12, 62, 82 without departing from the principles of the present invention. In particular, those changes which would be obvious to one of ordinary skill in the art are within the scope of, and are contemplated by, the principles of the present invention. For example, although the apparatus described herein have a light source positioned within a filtering portion and a light receiving device positioned exterior to the filtering portion, the light source could be easily positioned exterior to the filtering portion and the light receiving device could be positioned in the interior of the filtering device. Accordingly, the foregoing detailed description is to be clearly understood as being given by way of illustration and example only, the spirit and scope of the present invention being limited solely by the appended claims.

What is claimed is:

1. A method of inspecting a well screen having a sidewall portion, the method comprising the steps of:

providing a light source;

positioning the light source relative to the sidewall portion to direct light therethrough between inner and outer side surfaces of the sidewall portion;

providing a light sensor; and operating the light sensor to measure the light directed through the sidewall portion.

2. The method according to claim 1, wherein the step of providing a light sensor comprises providing a photoelectric sensor, and wherein the operating step further comprises positioning the photoelectric sensor proximate the sidewall portion.

3. The method according to claim 1, further comprising the steps of providing a circumferentially spaced apart series of light conducting members and positioning the light conducting members relative to the sidewall portion.

4. The method according to claim 3, wherein the light conducting members positioning step further comprises positioning the light conducting members circumferentially about an outer side surface of the sidewall portion.

5. The method according to claim 4, wherein the sidewall portion includes a helically disposed member having a pitch, and wherein the light conducting members positioning step further comprises spacing apart the light conducting members relative to the sidewall portion member pitch.

6. The method according to claim 3, further comprising the steps of providing a circumferentially spaced apart series of light intensifiers, and operating each of the light intensifiers to increase the intensity of the light directed through the sidewall portion to one of the light conducting members.

7. The method according to claim 1, further comprising the step of displacing the light source and light sensor simultaneously relative to the sidewall portion.

8. The method according to claim 7, further comprising the step of relating displacement of the light source and light sensor to the measurement of light directed through the sidewall portion.

9. The method according to claim 1, further comprising the step of interconnecting an instrument to the light sensor, the instrument being capable of operatively receiving an output of the light sensor.

10. The method according to claim 9, further comprising the step of utilizing the instrument to indicate when a quantity of light sensed by the light sensor exceeds a predetermined amount.

11. The method according to claim 1, wherein the light source positioning step further comprises disposing the light source within the well screen, wherein the light sensor operating step further comprises positioning a plurality of fiber optic lines circumferentially about an outer side surface of the sidewall portion opposite the light source and interconnecting the fiber optic lines to the light sensor, and further comprising the step of simultaneously displacing the light source and fiber optic lines relative to the sidewall portion.

12. A method of inspecting a generally tubular well screen having inner and outer side surfaces, the method comprising the steps of:

positioning a circumferentially disposed array of light receiving members relative to one of the inner and outer side surfaces;

positioning at least one light emitting device relative to the other of the inner and outer side surfaces; and measuring the amount of light transmitted between the inner and outer side surfaces.

13. The method according to claim 12, further comprising the step of interconnecting each of the array of light receiving members to at least one light sensor.

14. The method according to claim 13, further comprising the step of interconnecting an output of the light sensor to an instrument.

15. The method according to claim 14, wherein the measuring step further comprises providing a quantitative measurement of the intensity of light received by the light sensor.

16. The method according to claim 14, wherein the measuring step further comprises providing an indication of the intensity of light received by the light sensor relative to a predetermined intensity.

17. The method according to claim 12, further comprising the step of positioning a light intensifying device between the light transmitted between the inner and outer side surface and each of the array of light receiving members.

18. The method according to claim 12, further comprising the step of displacing the array of light receiving members and the light emitting device synchronously relative to the well screen.

19. A method of quantitatively measuring characteristics of a filtering portion of a well screen, the filtering portion having first and second opposite sides, the method comprising the steps of:

positioning a light source relative to the first side, so that light is directed through the filtering portion from the first side to the second side;

positioning a light intensity measuring device relative to the second side, so that the measuring device is capable of receiving the light directed through the filtering portion; and simultaneously displacing the light source and at least a portion of the measuring device across the respective first and second sides to thereby quantitatively measure the intensity of the light directed through the filtering portion.

20. The method according to claim 19, further comprising the step of providing the light intensity measuring device including a light sensor.

21. The method according to claim 20, wherein the light intensity measuring device providing step further comprises providing a plurality of light conducting members interconnected to the light sensor.

22. The method according to claim 21, wherein the light intensity measuring device positioning step further comprises positioning the light conducting members circumferentially about the second side.

23. The method according to claim 22, wherein the light conducting members positioning step further comprises axially spacing apart the light conducting members, such that the light conducting members are disposed in an array overlying a circumferentially extending surface area of the second side.

24. The method according to claim 23, wherein the displacing step further comprises displacing the measuring device portion to thereby displace the surface area of the second side overlaid by the array of light conducting members.

25. The method according to claim 19, further comprising the step of providing an indication when the quantitative measurement of light intensity directed through the filtering portion departs from a predetermined intensity range.

26. Apparatus for inspecting a well screen, the apparatus comprising:

a light intensity measuring device;

a light source; and a displacement device, the displacement device interconnecting the measuring device and the light source, and the displacement device synchronously displacing the measuring device and light source relative to the well screen in a manner transmitting light from the light source to the light intensity measuring device between inner and outer side surfaces of a sidewall portion of the well screen.

27. The apparatus according to claim 26, wherein the measuring device includes a light sensor.

28. The apparatus according to claim 27, wherein the light sensor is configured for complementary engagement with the well screen.

29. The apparatus according to claim 27, wherein the measuring device further includes at least one light conducting member interconnected to the light sensor.

30. The apparatus according to claim 29, wherein the light conducting member is capable of conducting light from a position proximate the well screen to a position remote from the well screen where the light conducting member is interconnected to the sensor.

31. The apparatus according to claim 29, wherein the measuring device includes a plurality of the light conducting members, and wherein the light conducting members are circumferentially spaced apart.

32. The apparatus according to claim 29, further comprising a housing configured for complementary engagement with the well screen, an end of the light conducting member being positioned within the housing.

33. The apparatus according to claim 26, wherein the light intensity measuring device includes a circumferentially and axially distributed array of light receiving members.

34. The apparatus according to claim 26, further comprising a light intensifying device positioned relative to the light intensity measuring device.

35. A hydraulic resistance measuring device for use with a filtering portion of a well screen, the device comprising:

at least one light source, the light source being capable of directing light through the filtering portion;

at least one light receiver positioned relative to the light source, the light receiver being capable of receiving the light directed through the filtering portion; and an instrument interconnected to the light receiver, the instrument providing an output indicative of the filtering portion hydraulic resistance when the light receiver receives the light directed through the filtering portion between inner and outer side surfaces thereof.

36. The device according to claim 35, further comprising a displacement device interconnected to the light source and light receiver, the displacement device being capable of displacing the light source and light receiver relative to the filtering portion.

37. The device according to claim 36, wherein the displacement device displaces the light source and light receiver simultaneously, so that the light receiver is continuously opposite the light source.

38. The device according to claim 35, wherein the instrument is configured to indicate whether the intensity of light received by the light receiver is within a predetermined range.

39. The device according to claim 35, further comprising a light intensifying device positioned between the light source and the light receiver.

40. The device according to claim 35, wherein the light receiver includes a light sensor mounted to a housing, the housing being configured for complementary engagement with the filtering portion.

41. The device according to claim 35, wherein the light receiver includes an array of light conducting members interconnected to a light sensor and mounted to a housing, the housing being configured for complementary engagement with the filtering portion.

42. The device according to claim 41, wherein ends of the light conducting members are circumferentially and axially spaced apart within the housing.

43. The device according to claim 42, wherein the ends of the light conducting members are further helically disposed within the housing.

* * * * *